(12) United States Patent
Svetliza

(10) Patent No.: US 6,178,340 B1
(45) Date of Patent: Jan. 23, 2001

(54) THREE-DIMENSIONAL INFRARED IMAGER FOR SUBCUTANEOUS PUNCTURE AND STUDY OF VASCULAR NETWORK

(76) Inventor: Eduardo Svetliza, 19/6 Anilevitz St., Raanana 43321 (IL)

(*) Notice: Under 35 U.S.C. 154(b), the term of this patent shall be extended for 0 days.

(21) Appl. No.: 09/138,542

(22) Filed: Aug. 24, 1998

(51) Int. Cl.[7] .................................................. A61B 1/00
(52) U.S. Cl. ..................... 600/310; 600/321; 600/407; 600/473; 600/476; 250/226; 250/341.8
(58) Field of Search ........................... 250/226; 128/664, 128/920; 348/65; 359/464; 600/310, 473, 476, 311, 312

(56) References Cited

U.S. PATENT DOCUMENTS

| | | | |
|---|---|---|---|
| 4,817,622 | * 4/1989 | Pennypacker et al. | 128/664 |
| 5,519,208 | * 5/1996 | Esparza et al. | 250/226 |
| 5,751,479 | * 5/1998 | Hamagishi et al. | 359/464 |
| 5,910,816 | * 6/1999 | Fontenot et al. | 348/65 |

\* cited by examiner

*Primary Examiner*—Marvin M. Lateef
*Assistant Examiner*—Jeoyuh Lin
(74) *Attorney, Agent, or Firm*—Edward Langer, Pat. Atty.

(57) ABSTRACT

A novel three-dimensional infrared imager for study of the vascular network so as to cause blood vessels to be visualized for accurate subcutaneous puncture during insertion of a hypodermic needle. The invention uses the properties of near infrared light as it is absorbed and reflected by the human body, allowing the user to visualize the tissues a few millimeters in depth from the skin's surface. The use of infrared light permits the manipulation of the acquired information to a grade of sensed visualization, which is impossible to reach with visible light. The invention imitates the human three-dimensional perception by use of a stereoscopic infrared viewer, and is designed to be user friendly, allowing the health care professional to work in his usual manner. A double image is superimposed on the viewer and the user wears blue-red eyeglasses to create the three-dimensional image from the double image on the viewer. With the depth perception provided by the three-dimensional image, the user can accurately penetrate the vein on the initial attempt, thereby lowering the fear of venous punture and causing the patient to be at ease, while lowering the incidence of medical complications associated with inaccurate puncture. In a preferred embodiment of the invention, a liquid crystal display (LCD) mounted in a frame is provided on the upper surface of the apparatus. Sensitive, charge-coupled devices are provided which develop images and deliver them to a microprocessor which synchronizes the images and allows the user to manipulate the images as desired, controlling effects such as brightness, contrast, sharpness and edge enhancement. In another embodiment, the inventive imaging system incorporates the use of a contrast agent to enhance the image and allow for study of the vascular system. In yet another embodiment, the imaging system incorporates the use of a coherent source of light, such as an infrared laser.

19 Claims, 5 Drawing Sheets

THREE-DIMENSIONAL INFRARED IMAGER FOR SUBCUTANEOUS PUNCTURE AND STUDY OF VASCULAR NETWORK

FIELD OF THE INVENTION

The present invention relates generally to instruments for infrared imaging, and in particular, to a system for imaging the vascular network in order to study it and to enable safe and accurate puncture of the veins by a hypodermic needle.

BACKGROUND OF THE INVENTION

Although insertion of needles into the human vascular network is commonly considered by medical professionals to be one of the most routine and easily performed activities, such a "simple" technique is traumatic, painful and dangerous for the patient. Erroneous attempts to penetrate the arterial-venous system are not rare in medical practice, causing numerous injuries to the patient.

Penetration of the vascular network is necessary for two main reasons: extraction of blood for laboratory analysis or delivery of fluids and/or different agents of contrast used in angiographic techniques. The consequences due to missed puncture of the vein include the need for repeated puncture causing the patient to feel further threatened, discomfort, pain, sweat, fear, and in difficult patients loss of cooperation while performing the puncture. Extravasation of agents of contrast due to a missed vein puncture can cause terrible pain, sweat and necrosis of the place of puncture in some cases.

Certain patient groups are known to be more difficult to properly puncture. The classical groups include: overweight people, young women, infants (especially premature babies) and young children, dark-skinned people and people in shock.

Apparatus for visualization of the subcutaneous vessels are known, and an example of current imaging technology is disclosed in U.S. Pat. No. 4,817,612 to Pennypacker et al, in which a two-dimensional vein location system is described. Working under a two-dimensional image causes more damage than working without an imager. Because there is no depth sensation, the access of the needle in relation to the arm will be incorrect, necessitating repetitive puncturing.

U.S. Pat. No. 5,519,208 to Esparza et al discloses a two-dimensional vein location system which requires the attachment of an LED to the tip of the needle. A light of this sort will be emitted tangentially, causing bad scattering of light on the area of inspection in relation to the optical axis of the human eye. If the infrared light comes from the wrong direction the light will not be able to provide the proper information. Infrared light which is applied to the human body must be scattered uniformly to distinguish the fine details of the veins before any electronic manipulation of the image has been done. Improper illumination cannot be corrected with the use of an image processor, since information which does not exist on the image because it has not been properly illuminated cannot be enhanced by any image processor. In addition the attachment of an LED to the tip of the needle necessitates providing a power source to feed the LED. Currently, disposable needles are used almost exclusively, making this design impractical.

U.S. Pat. No. 5,608,210 to Esparza et al mentions the visual sensation of three dimensions, although the apparatus described therein is unwieldy, and is designed to be worn on the head. This demands that the health care providers change their style of working. Although this method has been used in the indirect ophthalmoscope for more than 50 years, the modern instrument reaches a weight of only 300–350 grams. Attempts by many companies to introduce a more sophisticated head-worn opthalmoscope with a video system have resulted in failures due to the weight and the instability of the image due to head movement. These obstacles apply to a head-worn vascular imager as well. Other attempts at head-worn imagers include a military infrared viewer mounted on the head or worn on goggles. This device was rejected because the weight did not allow maintenance of a constant image in accordance with the optical axis of the eye.

Although the Esparza '210 patent does provide a certain three-dimensional sensation, the effect is actually more theoretical than practical as the distance from the eyes of the user to the subject must be fixed, otherwise the cameras need to be refocussed, so that both cameras are tilted to a convergent point on the subject. If the distance from the eyes of the user to the subject is reduced the convergent point is crossed and the three-dimensional effect is lost. In order to hold a video screen (or two) in front of the user's eyes, optical lenses are required with a refractive power which is determined so as to correct the shorter distance accepted by the human eye. This would cause discomfort to the user upon removal of the apparatus until the eyes would readjust to their normal focus. This discomfort could include dizziness, nausea and headaches.

Therefore, it would be desirable to provide an imager with proper illumination which would provide a clear three-dimensional image in real time so as to improve the success rate of health care providers in penetrating the vascular system. This would allow the patient to both feel at ease and comfortable, thereby lowering the stress level of patients who fear an inaccurate puncture and also lowering the incidence of medical complications resulting from an inaccurate puncture.

SUMMARY OF THE INVENTION

Accordingly, it is a principal object of the present invention to overcome the problems associated with the prior art and provide a novel three-dimensional infrared imager with a proper illumination source for study of the vascular network so as to cause blood vessels to be visualized for accurate subcutaneous puncture during insertion of a hypodermic needle. This apparatus would lower the fear of venous puncture and lower the incidence of medical complications associated with inaccurate puncture.

The invention is based on use of knowledge associated with the human vision system, in which both eyes are receptors of information transmitted by visible light. The rays of light are collected by the cornea and reach the lens of the eye which sends them to a common focussed point on the retina called the macula. The macula is the most sensitive part of the retina, and is responsible for the acute sight due to the largest concentration therein of the photoreceptors. The photoreceptors are connected with the neurons which convert light energy into electro-chemical pulses, which are transmitted by the nerve fiber layer through the optic nerve to the visual center located at the back of the brain. The collection of information by both eyes is transformed by the brain into a three-dimensional perception of the external world, and such perception relates to the visible portion of the light spectrum. Light wavelengths above or below the visible zone are not sensed by the eyes. Therefore, the use of sensors sensitive to infrared radiation and conversion to a visible image improves the human vision capability beyond its normal limitations.

The present invention uses the properties of near infrared light as it is absorbed and reflected by the human body allowing the user to visualize the tissues a few millimeters in depth from the skin's surface. The use of infrared light permits the manipulation of the acquired information to a grade of sensed visualization, which is impossible to reach with visible light.

The present invention is designed to be user friendly, allowing the health care professional to work in his usual manner. The invention imitates the human three-dimensional perception by use of a stereoscopic infrared viewer. A double image is superimposed on the viewer and the user wears blue-red glasses to create the three-dimensional image from the double image on the viewer. With the depth perception provided by the three-dimensional image, the user can accurately penetrate the vein on the initial attempt, causing the patient to be at ease.

In a preferred embodiment of the invention, a liquid crystal display (LCD) mounted in a frame is provided on the upper surface of the apparatus. Sensitive, charge-coupled devices are provided which develop images and deliver them to a microprocessor which synchronizes the images and allows the user to manipulate the images as desired, controlling effects such as brightness, contrast, sharpness and edge enhancement. Two sensors are provided fixed to the LCD. The support of the apparatus is flexible allowing free movement, or is provided as an articulated arm. The user moves the sensors together with the LCD to find the proper distance and angle of work. Alternatively, the sensors may be movable and provided independent of the LCD, while the LCD remains in a fixed position. LED lamps provide infrared radiation. A diffuser lens is provided for better diffusion of the light on the subject. The angle of radiation ranges between 45° and 90° depending on the diffuser lens. The homogeneous dispersion of the light increases the definition of the fine details of simulated veins. The apparatus may be attached to a table or be standing on the floor.

In another preferred embodiment, the LCD screen is separated from the frame and held on the wall or placed on a table or supported by an arm. The frame includes the infrared video sensors and the infrared illumination which is projected on the subject. In this way the user is able to work more comfortably.

In yet another embodiment, one illumination source and one diffuser lens are used for uniform scattering of radiation. Another aspect of the required radiation is provided as fiber optics, allowing the light reaching the subject to be soft and uniform.

In still a further embodiment, the inventive imaging system incorporates the use of a contrast agent which may be administered intravenously to obtain an angiogram in a three-dimensional image to allow for study of the vascular system.

In yet another embodiment, the imaging system incorporates the use of a coherent source of light, such as an infrared laser, provided in a double beam configuration for scanning and illumination, with a beam splitter optical arrangement.

Other features and advantages of the invention will become apparent from the following drawings and description.

BRIEF DESCRIPTION OF THE DRAWINGS

For a better understanding of the invention with regard to the embodiments thereof, reference is made, by way of example only, to the accompanying drawings in which like numerals designate corresponding elements throughout, and in which.

DETAILED DESCRIPTION OF THE PREFERRED EMBODIMENTS

Figure 1B:
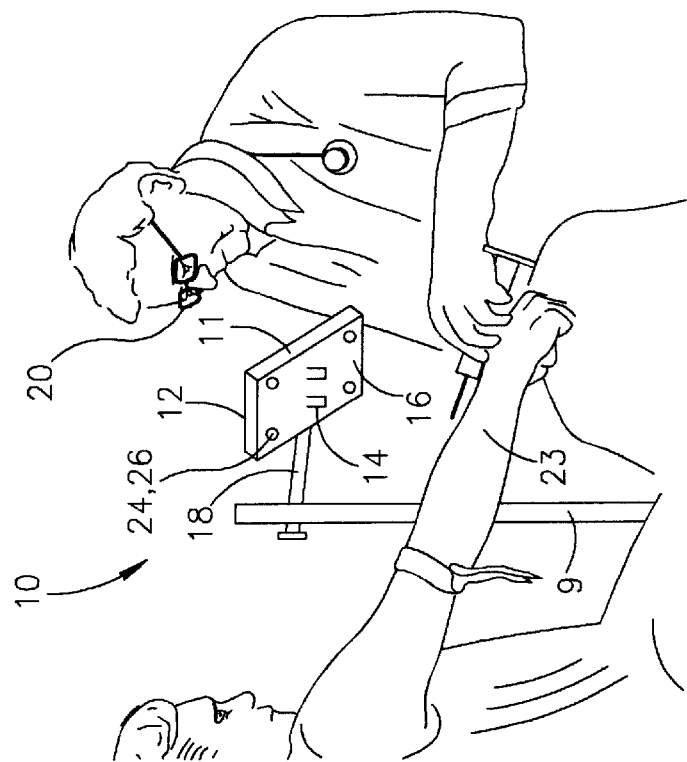
FIGS. 1a–b show, respectively, a health care provider attempting venous puncture without and with the apparatus of the present invention.
Figure 1A:
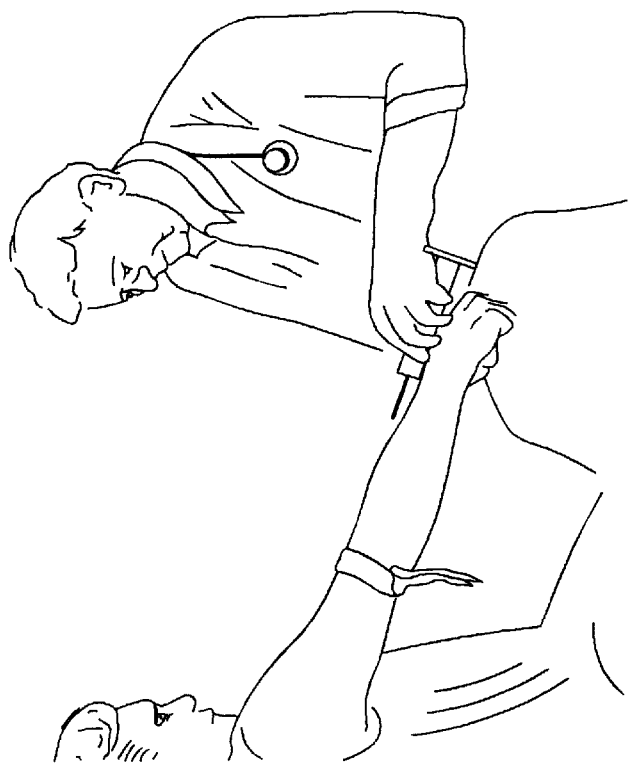

Referring now to FIG. 1a, there is shown a health care provider attempting venous puncture using the conventional method. In FIG. 1b the health care provider is using the apparatus 10 of the present invention to aid in location of the veins. Note that the position of the user is consistent with that used in the conventional method and the present invention allows the user to work in the manner to which he is accustomed. LCD screen 12 on apparatus 10 provides two superimposed images due to two infrared video sensors 14, 16 mounted on the back of screen 12 which obtain the images from different angles. Screen 12 is mounted within a frame 11 and its position can be conveniently adjusted with the use of articulated arm 18, mounted on stand 9. The user wears blue-red or other two color filter viewing eyeglasses 20 to perceive a three- dimensional infrared real time image of the veins 22 (FIG. 2), in an area of examination 23 on the skin.

Figure 2:
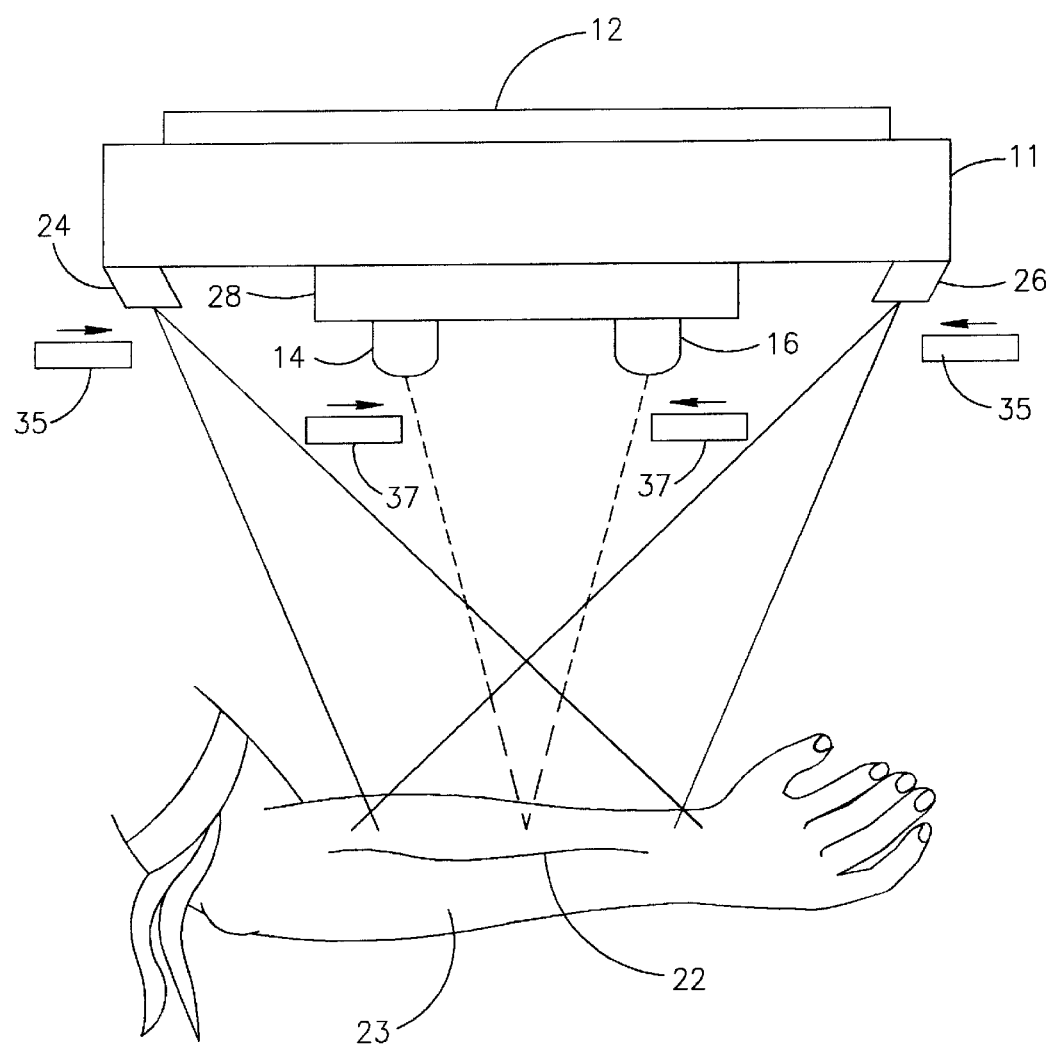
FIG. 2 shows a side view of the apparatus operated in accordance with the principles of the invention.

FIG. 2 shows a side view diagram of the apparatus operated in accordance with the principles of the invention. Infrared LED light sources 24 and 26 project light onto veins 22. Light which is reflected by the skin is sensed by sensors 14 and 16. Mounted below the lower side of LCD screen 12 is a microprocessor 28 which is programmed in accordance with skill of the art electronic imaging techniques to synchronize images delivered from sensors 14 and 16. Sensors 14 and 16 may be either black and white types, or color infrared sensors.

Microprocessor 28 also allows manipulation of the image to control the level of brightness, contrast, sharpness, edge enhancement, and subtraction. This is accomplished by means of knobs or pushbuttons on image control panel 30 visible in FIG. 4. The image can be converted to a negative image allowing the user to visualize the veins in white on a black background for further clarity. If sensors 14 and 16 are provided as color sensors, the color images are obtained by adjusting the color parameters of each sensor to the respective color desired. The color parameter of one sensor is adjusted to obtain a red image from a value of the red color zone, and the color parameter of the second sensor is adjusted to a green or blue color zone value.

If a third color sensor is added to the system, this will improve the color appearance of the image, and microprocessor 28 synchronizes the third color sensor, which may use the green or blue color, so that it blends with the image of the other two color sensors, to provide a full infrared color image.

Figure 3:
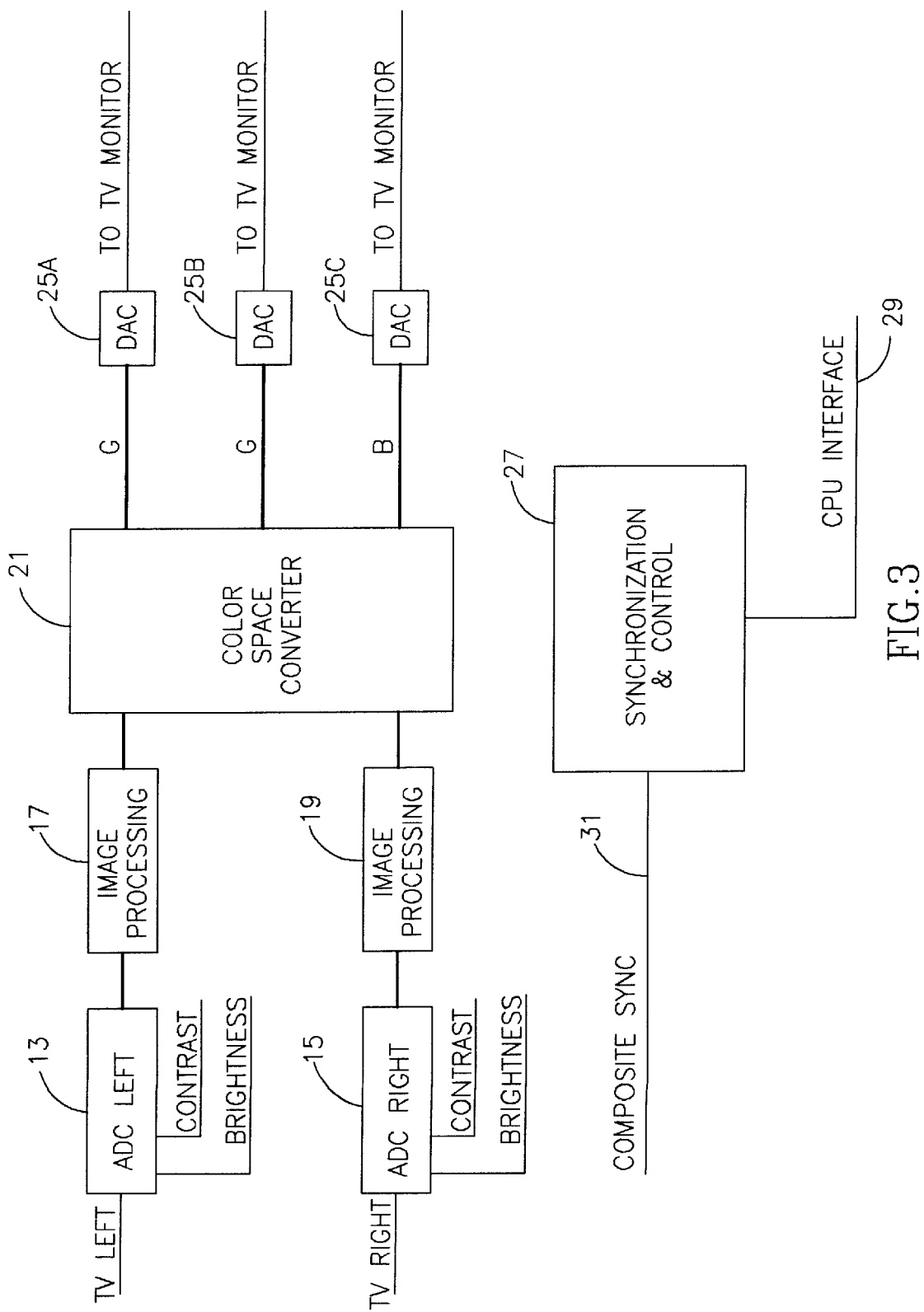
FIG. 3 is an electronic block diagram of a color converter circuit for use with the apparatus of FIG. 2.

If sensors 14 and 16 are provided as black and white TV cameras, it is possible to obtain color images from them by use of a color converter circuit, as shown in FIG. 3. Input from each TV camera (marked left and right) which has been adjusted for contrast and brightness is fed to A/D converters 13, 15 which digitize the signal. After digitalization, a digital signal from each camera is fed to image processing modules 17, 19. Image processing modules 17, 19 enable an inverted signal to be built, and perform edge enhancement and dilation, erosion filtering, etc. The output of image processing modules 17, 19 is used as an address and is fed to color space converter 21 which operates as a look-up table and enables the image to be shifted separately within a 24-bit color space. Color space converter 21 can also be used to simple processing purposes, such as intensity adjustment.

The output of color space converter 21 is fed to a set of D/A converters 25a–c, and each signal can be shown on an RGB video monitor. If the incoming TV signal fed to the conversion circuit in FIG. 3 has a different standard from the monitor frequency, additional buffer memory can be used to equalize the sweep rate of the signals. A composite synchronization signal 31, provided by synchronization and control unit 27, performs all synchronization in the circuit of FIG. 3, and both input TV cameras receive the same sync sequence. All components in the system are CPU-controllable via CPU interface 29.

Figure 4:
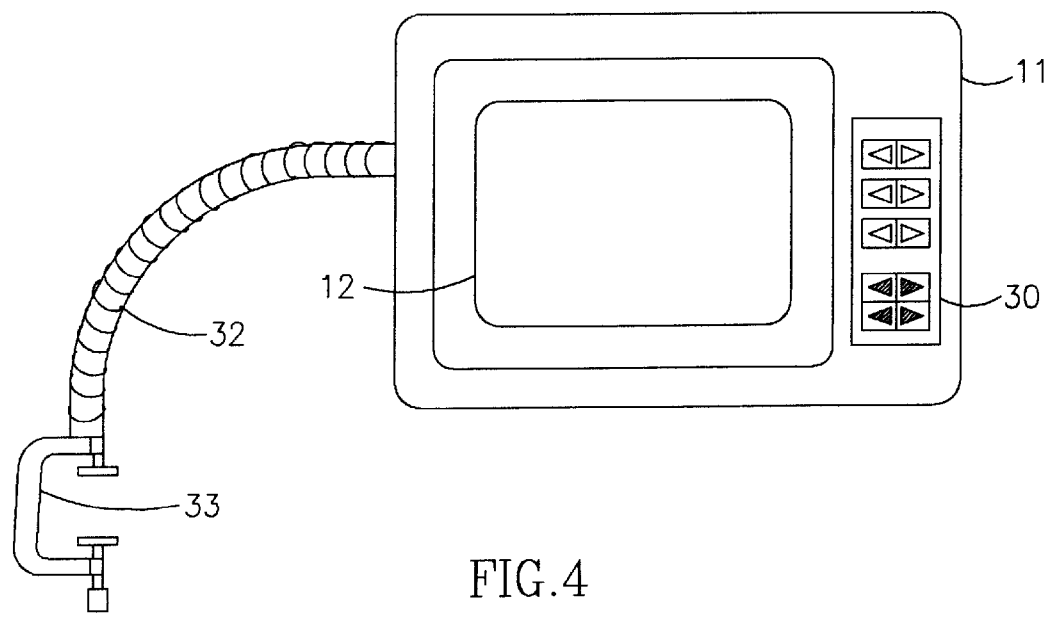
FIG. 4 is a schematic layout diagram of a three-dimensional infrared imager, constructed in accordance with the principles of the present invention.

FIG. 4 also shows an alternate embodiment of the apparatus in which the apparatus 10 is mounted on flexible arm 32 which can be bent in any direction. Other possible embodiments include providing the apparatus mounted on a table or wall, and attached by clamp 33 to a rigid support or supported by other types of arms.

Apparatus 10 can be designed to be portable, by use of a battery power source disposed in frame 11.

In yet another embodiment, screen 12 can be separated from frame 11 containing infrared video sensors 14, 16 and LEDs 24, 26. This allows the user freedom to select a comfortable working position. A wireless transmission technique can be utilized in which an RF transmitter is installed in the portion of apparatus 10 having the infrared sensors 14, 16 and the illumination source 24, 26. A video signal developed by sensors 14, 16 is transmitted via the RF transmitter, similar to a TV broadcast, to a receiver installed in the apparatus 10 portion having display screen 12.

In a further embodiment, one centrally-located illumination source and one diffuser lens are used to uniformly scatter the radiation about the cental optical axis. Additional radiation can come from fiber optics to provide soft and uniform light.

Figure 5:
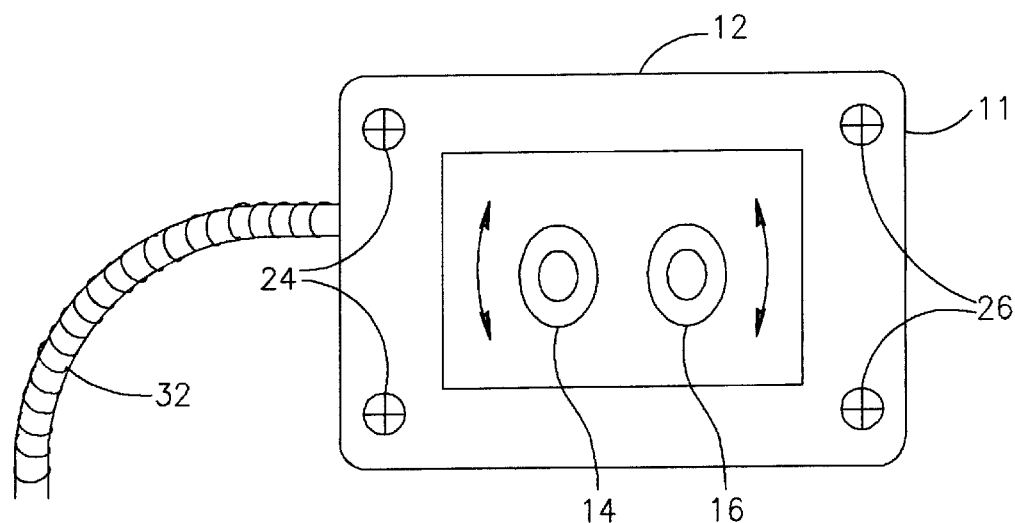
FIG. 5 illustrates an alternate embodiment of the present invention in which the sensors move independently of the main body of the apparatus.

Referring now to FIG. 5, there is shown an alternative embodiment in which infrared video sensors 14, 16 may be moved independently of screen 12 to allow the user to find the proper angle for imaging while allowing screen 12 to remain in a fixed comfortable viewing position. Infrared LED light sources 24, 26 located proximal to sensors 14, 16 supply light with an angle of radiation of between 45°–90°, dependent on the diffuser lens. This provides better diffusion of the light on the subject, allowing for clearer definition of the veins in the image.

In accordance with the principles of the present invention, apparatus 10 can be used as part of an infrared imaging system for study of the vascular network by using an agent of contrast called indocyanine green (ICG) to obtain an angiogram. The peak absorption of the fluorescent emission of ICG lies in the range of between 800–850 nm wavelength in the light spectrum. Apparatus 10 is upgraded by the addition of appropriate light filters (at arrows in FIG. 2), such as an exciter filter 35 at the illumination source 24, 26 and barrier filters 37 at the sensors 14, 16. This enables a new technique in visualization of the fluorescent emission of ICG, and the grade of energy emitted by the dye increases significantly the visualization of blood vessels which are deeper below the skin surface. This technique has been found suitable for study of the human arterio-venous circulation and perfusion of tissues.

The ICG compound is a water-soluble tricarboncyanine dye with a molecular weight of 775. The dye is excreted by the liver via bile, and its use in humans was approved by the US FDA about thirty years ago. The technique has been found satisfactory for recording dilution in blood and is used as an indicator of cardiac output. The dye was also used in the past for diagnosis of liver function and hepatic blood flow having a maximum absorption of 810 nm wavelength. The changing concentration of ICG in the blood was monitored by ear densitometry.

Other applications of the dye in the ophthalmic field enable performance of angiograms of the deeper layer of the retina called the choroid. Transmission of fluorescence energy in the infrared region by the pigment epithelium, which is a pigmented layer separating the retina vessels from the choroidal vessels, is more efficient than in the region of visible light energy.

Figure 6:
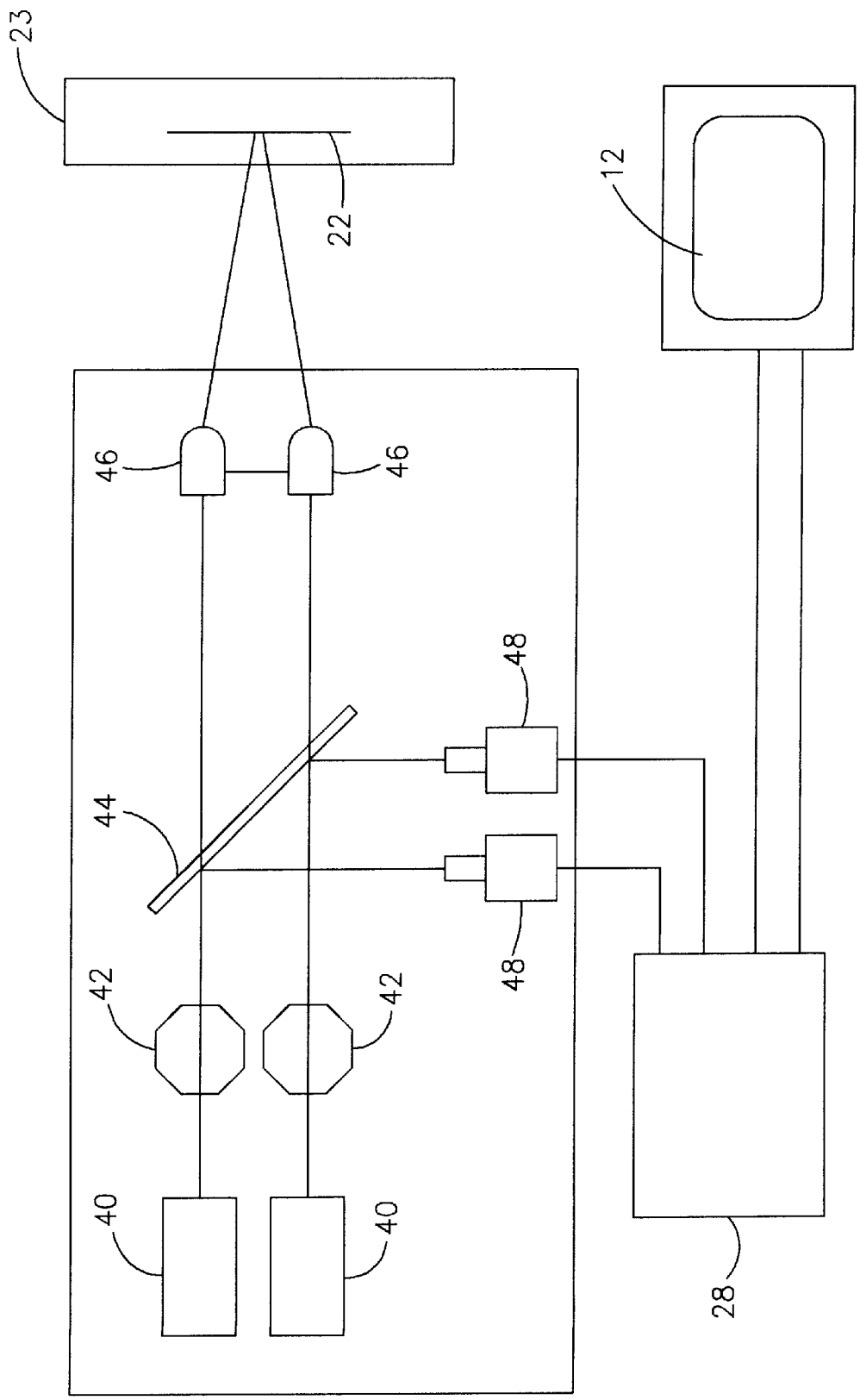
FIG. 6 illustrates another alternative embodiment of the invention using a double beam configuration for scanning and illumination of the area of interest.

In FIG. 6, there is illustrated another alternative embodiment of the invention using a double beam configuration for scanning and illumination of the objective. In this embodiment, two infrared coherent sources of light 40, such as a laser, are used to scan the fluorescent dye mentioned previously. Coherent light sources 40 are arranged in proximity to a double polygon combined reflector/galvanometer 42 which vibrates so as to control the light beam deflection for scanning in lateral and vertical directions, and direct it through beam splitter 44, and onto a pair of lenses 46, which focus each beam individually at the same point in the area of examination 23. The infrared coherent sources of light 40 may be provided by a laser scanner, such as that available commercially from General Scanning Inc., Somerville Mass. A single laser beam can be split via a beam splitter and mirror arrangement to provide the dual beams.

A pair of infrared detectors 48 collect the scanned information reflected through beam splitter 44, and the images are synchronized by microprocessor 28, and appear on LCD screen 12. Microprocessor 28 has the capability of causing disparity between the two images, for a suitable three-dimensional perception. Disparity of images means there is a difference between pixels of the superimposed images by separating them or magnifying one of them. Use of known pseudo-color techniques for processing the image in microprocessor 28 enables presentation of two colored images, similar to the technique described in connection with FIG. 3.

In summary, the present invention provides an effective, easy to use, three-dimensional infrared imager which allows the user to use conventional positioning techniques and will make the patient feel at ease when venous puncture is necessary. The invention also enables study of the vascular network using a fluorescent dye.

Having described the invention with regard to certain particular embodiments thereof, it is to be understood that the description is not meant as a limitation, since further modifications will now become apparent to those skilled in the art and it is intended to cover such modifications as fall within the scope of the appended claims.

I claim:

1. An apparatus for three-dimensional infrared imaging for subcutaneous puncture and study of the vascular network comprising:

at least one illumination means for illuminating the skin;

at least a pair of sensors for sensing light reflected by the skin;

processing means for developing a pair of differently colored images of the skin from said sensed reflected light, said illumination, means pair of sensors and processing means being integrated in a frame, a display means for displaying said pair of differently colored images provided by said processing means, in superimposed fashion;

a pair of color filter viewing eye glasses having different colored lenses, for simultaneously viewing said differently colored superimposed images on said display means, and perceiving said images as a real-time three dimensional image, and a means of supporting the apparatus in a manner independent of the subject and of the body of the user, thereby allowing the user to work in a conventional manner in performing the subcutaneous puncture and in a position consistent therewith.

2. The apparatus of claim 1 wherein said pair of differently colored images are two different colors, red and green.

3. The apparatus of claim 1 wherein each sensor of said pair of sensors is adjusted to only one color.

4. The apparatus of claim 1 further comprising a support stand and movable arm on which the apparatus is mounted, allowing for position adjustment against the skin.

5. The apparatus of claim 1 wherein said pair of sensors comprise black and white TV cameras, and wherein said processing means comprises means for converting black and white images produced by said black and white TV cameras to two color images.

6. The apparatus of claim 1 wherein said illumination means, pair of sensors, processing means and display means are mounted together in said frame which is supported independently of the body of the user.

7. The apparatus of claim 1 wherein said illumination means, pair of sensors, and processing means are mounted together in said frame, and said display means is mounted separately from said frame.

8. The apparatus of claim 7 wherein said display means is an LCD-type screen.

9. The apparatus of claim 7 wherein said display means is a screen other than an LCD-type.

10. The apparatus of claim 1 wherein said illumination means and pair of sensors are mounted in a first housing, and said processing means and display means are mounted in a second housing separate from said first housing.

11. The apparatus of claim 1 further comprising a portable power supply.

12. The apparatus of claim 1 further comprising an RF transmitter having input signals provided thereto by said pair of sensors for developing a video signal for transmission via said RF transmitter, said transmitted signal being received by a receiver providing an output signal for display on said display means.

13. The apparatus of claim 1 wherein said illumination means comprises a coherent light source.

14. The apparatus of claim 1 wherein said pair of sensors comprise detectors providing a video image.

15. The apparatus of claim 1 further comprising exciter filters mounted on said illumination source, and barrier filters mounted on said sensors, to enable visualization of a fluorescent image provided by a fluorescent dye circulating in the vascular network.

16. The apparatus of claim 1 wherein said processing means performs image processing by applying pseudo-color techniques for providing color images.

17. The apparatus of claim 1 wherein said illumination means comprises a double coherent beam of light provided in a scanner arrangement having an optical beam splitter for deflecting said reflected light to said pair of sensors.

18. The apparatus of claim 1 further comprising a third sensor and wherein said sensors comprise video cameras each adjusted to produce one of red, green and blue color images.

19. A method for three-dimensional infrared imaging for subcutaneous puncture and study of the vascular network, said method comprising the steps of:

illuminating the skin;

sensing light reflected by the skin;

processing in real-time and developing a pair of differently colored images of the skin from said sensed reflected light;

displaying said pair of differently colored images, in superimposed fashion;

simultaneously viewing said differently colored superimposed displayed images through a pair of color filter viewing eyeglasses, having different colored lenses, and perceiving. said images as a real-time three dimensional image, thereby allowing the user to work in a conventional manner in performing the subcutaneous puncture and in a position consistent therewith, wherein said illuminating, sensing, processing and displaying steps are performed by an apparatus which is independently supported and spaced apart from the skin of the subject and the body of the user, enabling a user to manipulate a hypodermic needle with both hands.

* * * * *